US007252973B1

(12) United States Patent
Goto et al.

(10) Patent No.: US 7,252,973 B1
(45) Date of Patent: Aug. 7, 2007

(54) PROTEIN AND PROCESSES FOR PRODUCING THE SAME

(75) Inventors: Masaaki Goto, Tochigi (JP); Akihiro Tomoyasu, Tochigi (JP); Kazuki Yano, Tochigi (JP); Fumie Kobayashi, Tochigi (JP); Nobuaki Nakagawa, Tochigi (JP); Hisataka Yasuda, Tochigi (JP); Kyoji Yamaguchi, Saitama (JP); Masahiko Kinosaki, Tochigi (JP); Shin-ichi Mochizuki, Tochigi (JP); Tadashi Nakarumai, Tochigi (JP); Tomonori Morinaga, Tochigi (JP); Eisuke Tsuda, Tochigi (JP); Kanji Higashio, Saitama (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/647,907

(22) PCT Filed: Apr. 9, 1999

(86) PCT No.: PCT/JP99/01906

§ 371 (c)(1),
(2), (4) Date: Dec. 4, 2000

(87) PCT Pub. No.: WO99/53056

PCT Pub. Date: Oct. 21, 1999

(30) Foreign Application Priority Data

Apr. 10, 1998 (JP) .................................. 10-099741
Aug. 28, 1998 (JP) .................................. 10-243355

(51) Int. Cl.
*C12P 21/04* (2006.01)
*C12N 5/02* (2006.01)
*C07K 1/00* (2006.01)

(52) U.S. Cl. ..................... 435/70.1; 435/374; 435/402; 530/350; 530/412; 530/413; 530/416

(58) Field of Classification Search ................ 514/2; 530/300, 350, 412, 413, 415, 416; 435/70.1, 435/374, 402, 71.1
See application file for complete search history.

(56) References Cited

U.S. PATENT DOCUMENTS 4,514,499 A * 4/1985 Noll
5,994,103 A * 11/1999 Olsen et al.
6,171,822 B1 * 1/2001 Kuestner et al.
6,538,119 B2 * 3/2003 Billing-Medel

OTHER PUBLICATIONS

Moore et al (Horm Met research, 1999, vol. 31, pp. 406-414.*
Mathews and Van Holde, Biochemistry, 1996, pp. 165-171.*
Matthews, B. Genetic and Structural Analysis of the Protein Stability Problem.*
Kim et al, PNAS, 1994.*
Frish et al (Biol. Chem., Hoppe-Seyler, 1994, 375:353-356.*
Burgess et al (Journal of Cell Biology, 1990, vol. 11, pp. 2129-2138).*
Lazar et al (Molecular and Cellular Biology, 1988, 8:1247-1252).*
Bowie et al. (Science, 1990, 257:1306-1310).*
Mathews and Van Holde, Biochemistry, 1996, pp. 166, figure 6.1.*
Robeva et al (Biochemical Pharmacology, 1996, vol. 51, pp. 545-555).*
Stedman's Medical dictonary, 2000, 27th Edition, definition of "fibroblast".*
Abstract of Ehler et al, Cell Motility and the Cytoskelton, 1996, vol. 34, pp. 288-298).*
Vogel et al (Journal of Biological Chemistry, 1981, vol. 256, pp. 13235-13242).*
Johnson and Tracey, 'Peptide and Protein Drug Delivery', In: Encyclopedia of Controlled Drug Delivery, vol. 2, 1999, pp. 816-833.*
Ishibashi, et al., Molecular Cloning of a Second Human Stanniocalcin Homologue (STC2), 1998, Biochemical and Biophysical Research Communication, Art. RC99300, 250, 252-258.
Chang & Redell, Identification of a second stanniocalcin cDNA in mouse and human: Stanniocalcin 2, MCE, 141 (1998) 95-99.
Levin, et al., Decreased food intake does not completely account for adiposity reduction after ob protein infusion, Feb. 1996, Proc. Natl. Acad. Sci. USA, vol. 93, pp. 1726-1730.
Sainsbury, et al., Intracerebroventricular administration of neuropeptide Y to normal rats increases obese gene expression in white adipose tissue, Diabetologia (1996) 39: 353-356.
A.C.-M. Chang, et al., "Identification of a Second Stanniocalcin CDNA in Mouse and Human: Stanniocalcin 2", Molecular and Endocrinology, 141, 1998, pp. 95-99.

* cited by examiner

*Primary Examiner*—Karen A. Canella
(74) *Attorney, Agent, or Firm*—Oblon, Spivak, McClelland, Maier & Neustadt, P.C.

(57) ABSTRACT

A novel protein and a process of producing the protein is provided. The protein is a glycoprotein having activity of suppressing the differentiation and/or maturation of adipocyte, having a molecular weight of about 45 kD under non-reducing conditions and about 28 kD and/or 23 kD under reducing conditions, and exhibiting affinity to heparin. A process of producing the protein comprising culturing human fibroblasts and purifying the culture broth by chromatography using an ion exchange column, affinity column, and reverse phase column.

A cDNA encoding the protein and a process of producing the protein using the cDNA are also provided. The protein of the present invention is useful as a pharmaceutical composition for preventing or treating obesity or as an antigen for establishing immunological diagnosis, etc.

8 Claims, 4 Drawing Sheets

PROTEIN AND PROCESSES FOR PRODUCING THE SAME

TECHNICAL FIELD

The present invention relates to an adipogenesis inhibitory factor (ADIF) which is a novel protein having an activity of suppressing differentiation and/or maturation of adipocytes, and to methods for producing the same.

The protein of the present invention is useful as a pharmaceutical composition for preventing or treating obesity or as an antigen for establishing immunological diagnosis.

BACKGROUND ART

Obesity is a risk factor of diseases such as diabetes mellitus, hypertonia, and heart disease, which threaten health of people in advanced countries. Obesity means physical conditions wherein adipose tissues have abnormally accumulated. Adipose tissues are special organs wherein surplus in vivo energies are stored as fat or triglyceride, and constructed of fibroblasts including adipocytes and their precursors, macrophages, blood vessel surrounding cells, blood cells, and the like.

Adipocytes are said to amount from ⅓ to ⅔ of cells which are present in adipose tissues and to accumulate fats or triglycerides therein. Adipocytes differentiate and mature through the process starting from mesenchymal multipotent stem cells, and growing into lipoblasts which have acquired a base as adipocytes, precursor adipocytes with no lipid droplets but having initial markers of adipocytes, immatured adipocytes containing lipid droplets, and finally into matured adipocytes containing a large quantity of accumulated fats. Adipocytes of adults suffering from slight obesity hypertrophically grow due to increase in the amount of accumulated triglyceride. Number of adipocytes increases as the degree of obesity becomes conspicuous. Therefore, decreasing the number of adipocytes by controlling differentiation and maturation or suppressing hypertrophia of matured adipocytes are expected to stop progress of obesity by suppressing the increase in the amount of accumulated fats, and to treat obesity. Control of in vivo adipocyte differentiation has been proven to undergo either positively or negatively according to a number of factors derived from environmental factors such as ingestion, exercise, and so on. As cytokines which control differentiation of adipocytes from adipocyte precursors, tumor necrosis factor-α (TNF-α: Torti F. M. et al., Science, Vol. 229, p 867 (1985)), transforming growth factory-β (Ignotz R. A. et al., Proc. Natl. Acad. Sci. USA, Vol. 82, p 8530 (1985)), preadipocyte factor-1 (Pref-1: Smas C. M. et al., Cell, Vol. 73, p 725 (1993)), and the like have been reported. In addition, leptin, the translational product of an ob gene which has recently been cloned, has been reported to possibly decrease the intake amount and the weight of adipose tissues via central nerve system (Levin N. et al. Proc. Natl. Acad. Sci. USA, Vol. 93. P 1726, 1996).

Furthermore, intracerebral peptide-neuropeptide Y which exhibits a strong appetite stimulating effect and its receptor are gathering attention as materials for the development of an obesity suppressing pharmaceutical (Sainsburg A. et al, Diabetologia, Vol. 39, p 353, 1996). These cytokines are expected to become a therapeutic agent for obesity due to their adipocyte depressing action on accumulation of fat. Clinical tests as an obesity therapeutic or preventive agent is ongoing on some of these cytokines such as leptin.

At present, one obesity therapeutic or preventive agent is commercially available in the USA under the Redux™ (American Home Products Co.). Other drugs such as Meridia (Kunol Co.) and Xenical (Roche Co.) will be approved as an obesity treating agent or a fat absorption inhibitor in the USA. The treatments method using these pharmaceuticals, however, are not necessarily satisfactory in the effects and therapeutic results. Development of a new agent which is available exhibits for these pharmaceuticals higher curative effect and less side effect usable have been desired.

DISCLOSURE OF THE INVENTION

As a result of extensive exploration to discover a novel compound having an anti-obesity effect or an obesity controlling effect, the present inventors have found a protein exhibiting an adipogenesis inhibitory activity, that is an activity of suppressing differentiation and/or maturation of adipocytes, in a culture broth of human embryo pulmonal fibroblast IMR-90 (deposited with ATCC, deposition No. CCL186). The present inventors have further found a process for accumulating this protein in a high concentration by culturing the cells using alumina ceramic pieces as a cell matrix and for purifying the protein efficiently. Moreover, the present inventors have also established an efficient method for isolating the protein from above-mentioned culture broth repeating adsorption and elution by sequentially with an ion exchange column, affinity column, and reverse phase column.

Specifically, an object of the present invention is to provide an adipogenesis inhibitory factor (ADIF) which is a novel protein having an activity of suppressing differentiation and/or maturation of adipocytes, and to a process of producing the protein from a culture broth obtained by culturing human fibroblasts.

Another object of the present invention is to provide a cDNA encoding the protein and a process of producing the protein using the cDNA.

As described above, the present invention relates to an adipogenesis inhibitory factor (hereinafter called "ADIF" from time to time) which is a novel protein having an activity of suppressing differentiation and/or maturation of adipocytes, and to a process of producing the protein.

The protein of the present invention has the following characteristics:
  a. Activity: suppresses differentiation and/or maturation of adipocytes,
  b. Molecular weight (by SDS-polyacrylamide gel electrophoresis):
    has a molecular weight approximately 45 kD under non-reducing conditions, and approximately 28 kD and/or 23 kDa under reducing conditions,
  c. Affinity: has affinity to heparin, and
  d. contains sugars.

The method for obtaining the protein of the present invention comprises culturing human fibroblasts and purifying the culture broth by chromatography using an ion exchange column, affinity column, and reverse phase column.

In the present invention, the protein can also be produced the protein from by culturing the human fibroblasts using alumina ceramic pieces as the cell culturing matrices.

Furthermore, the present invention relates to a cDNA encoding the protein. Moreover, the present invention relates to a process of producing the protein using the cDNA.

The protein of the present invention is useful as a pharmaceutical composition for preventing or treating obesity or as an antigen for establishing immunological diagnosis.

(Explanation of Symbols)
Lane 1: Molecular weight marker (SDS-PAGE under non-reducing conditions)
Lane 2: ADIF (SDS-PAGE under non-reducing conditions)
Lane 3: Molecular weight marker (SDS-PAGE under reducing conditions)
Lane 4: ADIF (SDS-PAGE under reducing conditions)

Figure 6:
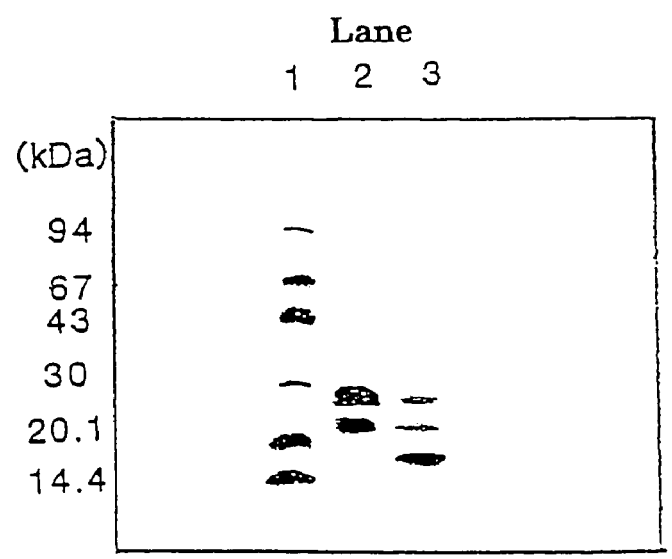

FIG. 6 shows SDS-PAGE after the finally purified product was treated with N-glycanase.

Figure 7:
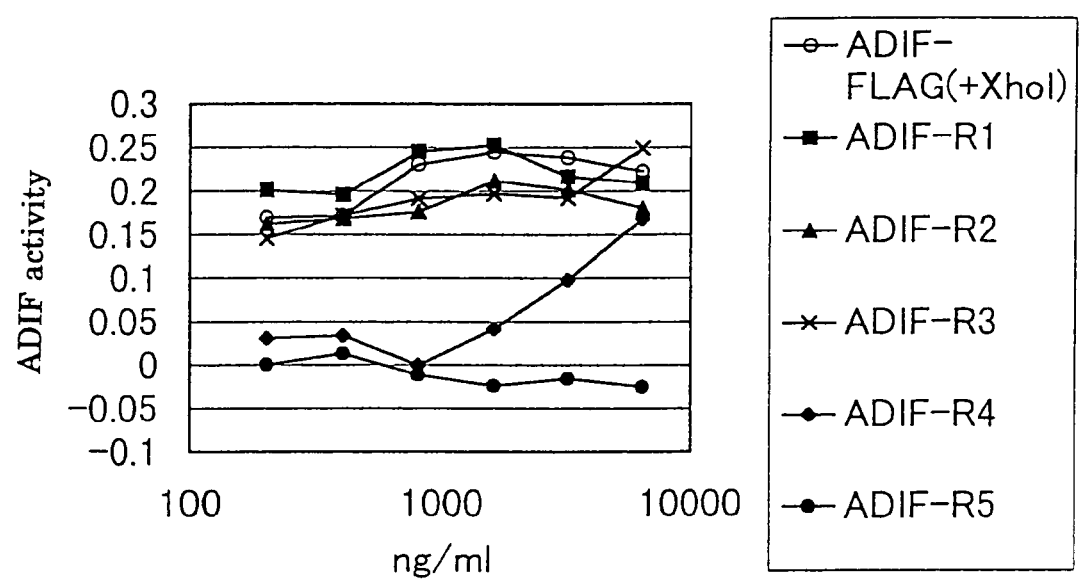

(Explanation of Symbols)
Lane 1: Molecular weight marker
Lane 2: Non-treated ADIF
Lane 3: ADIF which was treated to remove N-binding type sugar chains by N-glycanase FIG. 7 shows ADIF activity of Example 16.

BEST MODE FOR CARRYING OUT THE INVENTION

The present invention relates to an ADIF protein having activity of suppressing differentiation and/or maturation of adipocytes, originating from human fibroblasts, having a molecular weight by SDS-PAGE of about 45 kD under non-reducing conditions, about 28 kD and/or 23 kD under reducing conditions, and exhibiting affinity to heparin. The ADIF protein of the present invention has an apparent molecular weight of about 18 kD by SDS-PAGE under reducing conditions if N-binding type sugar chains are removed by N-glycanase treatment. The protein ADIF of the present invention suppress the process of differentiation and/or maturation of lipoblasts, precursors of adipocyte or immatured adipocytes, to matured adipocytes containing a large quantity of accumulated fats. The protein ADIF of the present invention clearly differs from known adipogenesis inhibitory factors in the molecular weight or the N-terminal amino acid sequence.

The present invention relates to a process for producing the protein ADIF comprising culturing human fibroblasts, applying the culture broth to a heparin column, eluting adsorbed fractions, loading the fractions on a cation exchange column and eluting the adsorbed fractions, and further treating the fractions with an anion exchange column, gel filtration column, and reverse phase column, thereby purifying and collecting the protein ADIF.

The column treatment in the present invention include not only the treatment of causing a culture broth to flow through a heparin sepharose column or the like, but also a treatment bringing about the same effect as the column treatment such as mixing and stirring the culture broth with heparin sepharose or the like by a batch process ("column treatment" in the present invention is used in this meaning).

In the present invention, the protein can also be efficiently produced by culturing the human fibroblasts using alumina ceramic pieces as a cell adhering carrier.

In addition, the present invention relates to a cDNA encoding the protein ADIF, the protein ADIF obtained by genetic engineering using the cDNA, and a process for producing the protein ADIF.

ADIF which is the protein of the present invention can be efficiently isolated and purified from a culture broth of human fibroblasts. Although there are no specific limitations to the human fibroblasts used as the production cell, human embryo pulmonal fibroblast IMR-90 (deposited with ATCC, deposition No. CCL186) is particularly preferable. The human fibroblast is caused to adhere to alumina ceramic pieces and static-cultured in a Dulbecco's modified Eagle medium (DMEM) to which cattle neonatal serum is added in a T-flask or a roller bottle for one week to ten days. The protein ADIF of the present invention is isolated and purified from this culture broth. As a method of isolation and purification, various purification processes can be carried out using of physical or chemical characteristics of the target protein ADIF according to conventional methods which are used for purification of proteins from biological samples. As a method of concentration, conventional methods such as ultrafiltration, freeze-drying, salting-out, and the like can be used. As a purification means, various purification operations commonly used for the purification of proteins, such as ion-exchanged chromatography, affinity chromatography, gel filtration chromatography, hydrophobic chromatography, reverse phase chromatography, preparative electrophoresis, and the like can be used either independently or in combination. A surfactant may be added when the protein of the present invention is purified from the culture broth. Although there are no specific limitations to the surfactant used in this instance, 0.1% CHAPS (3-[(3-cholamidopropyl)-dimethylammonio]-1-propanesulfonate), 0.01% polysorbate 80, or 0.01% polysorbate 20 is preferably used. Particular preferably, the protein ADIF of the present invention can be isolated and purified by processing the culture broth in the order of a heparin column, SP-cation exchange column, Q-anion exchange column, gel filtration column, heparin column, weak cation exchange column, and reverse phase column. The protein ADIF of the present invention thus obtained can be specified by the following biological and physicochemical characteristics:

(a) Activity: suppresses differentiation and/or maturation of adipocytes,
(b) Molecular weight (by SDS-PAGE): has a molecular weight of about 45 kD under non-reducing conditions, and about 28 kD and/or 23 kD under reducing conditions,
(c) Affinity: has affinity to heparin,
(d) contains sugars,
(e) N-terminal amino acid sequence (Sequence ID No. 2):

```
Xaa Ser Gln Gln Lys Gly Arg Leu Ser Leu Gln Asn Thr
1               5                   10

Ala Glu Ile Gln His Cys Leu Val Asn Ala Gly Asp Val
    15                  20                      25
```

```
                     -continued
Gly Cys Gly Val Phe Glu Cys Phe Glu Asn Asn Xaa Xaa
            30              35

Glu
40
```

(Xaa indicates an unidentified amino acid.)

The ADIF protein of the present invention can also be produced by a genetic engineering technique. Specifically, a cDNA encoding this protein is cloned based on the information of the amino acid sequence of natural ADIF obtained in accordance with the above-described method, and this cDNA is caused to express a gene recombinant ADIF by a genetic engineering technique. More specifically, the N-terminal amino acid sequence of the natural ADIF obtained by the present invention is analyzed and a mixture of oligonucleotides which can encode this sequence is prepared. Next, ADIF cDNA fragments are acquired by the PCR method (preferably the RT-PCR method) using the oligonucleotide mixture as a primer. The whole length cDNA of ADIF can be obtained by cloning the cDNA library prepared from IMR-90 cells using the cDNA fragments as a probe (Sequence Table, Sequence ID No. 12).

A gene recombinant ADIF protein can be obtained by inserting the resulting whole length cDNA into an expression vector to produce an ADIF expression plasmid, inserting the plasmid into various microorganisms or animal cells, and causing the ADIF to be expressed. The gene recombinant ADIF thus obtained has the same physicochemical characteristics as the above-described natural ADIF and its N-terminal amino acid sequence is shown as follows (the same sequence is shown in the Sequence Table, Sequence ID No. 3).

N-terminal amino acid sequence (Anticipated from cDNA; Sequence ID No. 3):

```
Ser Ser Gln Gln Lys Gly Arg Leu Ser Leu Gln Asn Thr
1               5                   10

Ala Glu Ile Gln His Cys Leu Val Asn Ala Gly Asp Val
        15              20                  25

Gly Cys Gly Val Phe Glu Cys Phe Glu Asn Asn Ser Cys
            30              35

Glu
40
```

The biological activity of ADIF can be determined by estimating the suppression effects of adipogenesis induced by dexamethasone with retardation of triglyceride accumulation using a mouse pre-adipocytic cell as a target according to the method of Kodama H. et al. (Journal of Cellular Physiology, Vol. 112, p 83 (1982)).

The adipogenesis inhibitory factor (ADIF) which is the protein of the present invention is useful as a pharmaceutical composition for preventing or treating obesity or as an antigen for establishing immunological diagnosis. ADIF can be administered safely to human being and animals. ADIF can be made into a preparation and administered either orally or parenterally. Examples of the pharmaceutical composition include compositions for injection, drip infusion, suppository, nasal agent, sublingual agent, percutaneous absorption agent, and the like. These compositions are formulated according known pharmaceutical preparation methods using pharmaceutically acceptable carriers, vehicles, stabilizers, coloring agents, surfactants, and/or other additives, and made into target preparations. When preparing compositions for injection, a pharmacologically effective amount of the adipogenesis inhibitory factor of the present invention may be mixed with a pharmaceutically acceptable vehicles or activation agents, such as amino acids, saccharides, cellulose derivatives, and other organic/inorganic compounds. In addition, when preparing a composition for injection from the adipogenesis inhibitory factor of the present invention and such vehicles or activation agents, a pH adjusting agent, buffering agent, stabilizer, solubilizing agent, and the like, may be added according to a conventional method as required.

EXAMPLES

The present invention will now be described in more detail by way of examples as follows. However it should be noted that the examples simply show illustration and the invention not restricted to them.

Example 1

(Preparation of Human Fibroblast IMR-90 Culture Broth)

Human fetal lung fibroblast IMR-90 (deposited with ATCC, deposition No. CCL186) was cultured on 80 g of alumina ceramic pieces (alumina: 99.5%, made by Toshiba Ceramic Corp.) and cultured in roller bottles (490 cm$^2$, 110×171 mm, made by Corning Co.). The culture was carried out using 40 roller bottles, each containing 500 ml of DMEM supplemented with 5% cattle neonatal blood serum and 10 mM HEPES (Gibco BRL), at 37° C. in the presence of 5% $CO_2$ for 7 to 10 days without rotating the bottles. After culturing, the culture broth was harvested and fresh medium was added to complete a culture cycle. 20 l of IMR-90 culture broth was obtained for each culture cycle. The culture broth was designed as Sample 1.

Example 2

(Measurement of Adipocyte Formation Suppressing Activity)

The activity of the ADIF which is the protein of the present invention was measured according to the method of Kodama H. et al. (Journal of Cellular Physiology, Vol. 112, p 83, (1982)). Specifically, the suppressing activity was determined by estimating adipogenesis induced by dexamethasone with triglyceride accumulation using a mouse pre-adipocytic cell MC3T3-G2/PA6 (RIKEN GENE BANK, RCB1127) as a target. Specifically, 50 µl of a sample diluted with α-MEM (Gibco BRL) containing 10% fatal bovine serum was filled in a 96 well microtiter plate. Mouse pre-adipocytic MC3T3-G2/PA6 cells were suspended in α-MEM containing $2×10^{-7}$ M dexamethasone and 10% fatal bovine serum, inoculated into the microtiter plate to a cell concentration of $3×10^3/50$ µl/well, and incubated for one week under the conditions of 5% $CO_2$, 37° C., and 100% humidity. After seven days, the medium was removed by aspiration and the cells were dried to measure the amount of triglyceride accumulated in the adipocytes using a triglyceride assay kit (Triglyceride G-Test Wako, manufactured by Wako Pure Chemicals Co., Ltd.). The reduction of OD at 510 nm was taken as the ADIF activity.

Example 3

(Purification of ADIF)

i) Purification on a Column of Heparin-Sepharose CL-6B

About 60 l of IMR-90 culture broth (Sample 1) was filtered with a 0.22 μm filter (Hydrophilic Milldisk, 2,000 cm$^2$, manufactured by Millipore Co.) and divided into three parts. Each part (20l) was applied to a heparin-sepharose CL-6B column (5×4.1 cm, gel volume 80 ml) equilibrated with a 10 mM Tris-HCl buffer containing 0.3 M NaCl (pH 7.5). After washing the column with 10 mM Tris-HCl buffer (pH 7.5) (hereinafter called "Tris-HCl") at a flow rate of 500 ml/hr, the sample was eluted with Tris-HCl containing 2 M NaCl (pH 7.5) to obtain 1.5 l of a heparin-sepharose CL-6B adsorbed fraction, which is designated as Sample 2.

ii) Purification on a Column of HiLoad-SP/HP

The heparin-sepharose adsorbent fraction (Sample 2) was dialyzed against 10 mM Tris-HCl (pH 7.5), supplemented with CHAPS to a final concentration of 0.1%, incubated at 4° C. overnight and divided into six parts. Each part was then applied to a cation exchange column (HiLoad-SP/HP, 2.6×10 cm, Amasham-Pharmacia Biotech Co.) equilibrated with 50 mM Tris-HCl containing 0.1% CHAPS(pH 7.5). After washing the column with 50 mM Tris-HCl (pH 7.5) containing 0.1% CHAPS, the adsorbed protein was eluted with a linear gradient of 0 to 0.5 M NaCl over in 120 minutes at a flow rate of 6 ml/min and fractions of 12 ml in size were collected. Using 30 μl of the each fraction, ADIF activity was measured by according to method described in Example 2 ADIF active fractions (936 ml) eluted at NaCl concentrations from about 0.15 to 0.25 M was obtained and was designated as Sample 3.

iii) Purification on a Column of HiLoad-Q/HP

The resulting Sample 3 was diluted with 1900 ml of 10 mM Tris-HCl (pH 7.5) containing 0.1% CHAPS and was divided into six parts. Each part was applied to a cation exchange column (HiLoad-Q/HP, 2.6×10 cm, Amasham-Pharmacia Biotech Co.) equilibrated with 50 mM Tris-HCl containing 0.1% CHAPS (pH 7.5). After washing the column with 50 mM Tris-HCl (pH 7.5) containing 0.1% CHAPS, the adsorbed protein was eluted with a linear gradient of 0 to 0.5 M NaCl over 120 minutes at a flow rate of 6 ml/min and fractions of 12 ml in size were collected. Using 30 μl of the each fraction ADIF activity was measured according to the method described in Example 2. A fraction (936 ml) eluted with NaCl concentrations from about 0.1 to 0.18 M was found to have ADIF activity and was designated as Sample 4.

iv) Purification on a Column of iLoad-SP/HP

The resulting Sample 4 was diluted with 1900 ml of 50 mM BisTris-HCl(pH 6.0) containing 0.1% CHAPS and was divided into three parts. Each part was applied to a cation exchange column (HiLoad-SP/HP, 2.6×10 cm, Amasham-Pharmacia Biotech Co.) equilibrated with 50 mM BisTris-HCl containing 0.1% CHAPS (pH 6.0). After washing the column with 50 mM BisTris-HCl (pH 6.0) containing 0.1% CHAPS, the adsorbed protein was eluted with a linear gradient of 0.1 to 0.6 M NaCl over 100 minutes at a flow rate of 6 ml/min and fractions of 12 ml in size were collected. Using 30 μl of the each fraction, ADIF activity was measured according to the method described in Example 2. A fraction (360 ml) eluted at NaCl concentrations from about 0.3 to –0.45 M was found to have ADIF activity and was designated as Sample 5.

v) Purification on a Column of Resource S

The resulting Sample 5 was diluted with 1,080 ml of 50 mM BisTris-HCl(pH 6.0) containing 0.1% CHAPS was divided into three parts. Each part was applied to cation exchange column (Resource S, 0.5×5 cm, Amasham-Pharmacia Biotech Co.) equilibrated with 50 mM BisTris-HCl containing 0.1% CHAPS (pH 6.0) in three portions. After washing the column with 50 mm BisTris-HCl (pH 6.0) containing 0.1% CHAPS, the adsorbed protein was eluted with a linear gradient of 0 to 0.6 M NaCl over 40 minutes at a flow rate of 1 ml/min and fractions of 1 ml in size were collected. Using 10 μl of the each fraction, ADIF activity was measured according to the method described in Example 2. A fraction (30 ml) eluted at NaCl concentrations from about 0.2 to 0.3 M was found to have ADIF activity and was designated as Sample 6.

vi) Purification on a Column of Superose 12

The resulting Sample 6 was concentrated using a centrifugal concentrator (Centricon 10, Millipore Co.) to about 600 μl and was divided three parts. Each part was applied to a gel filtration column (Superose 12, 1.0×60 cm, Amasham-Pharmacia Biotech Co.) equilibrated with 50 mM Tris-HCl containing 0.1% CHAPS and 0.5 M NaCl (pH 7.5). The proteins were developed with 50 mM Tris-HCl containing 0.1% CHAPS and 0.5 M NaCl (pH 7.5) at a flow rate of 0.5 ml/min and fractions of 0.5 ml in size were collected. Using 10 μl of the each fraction, ADIF activity was measured according to the method described in Example 2. A fraction (9 ml) developed at between about 25 to 30 minutes was found to have ADIF activity and was designated as Sample 7.

vii) Purification on a Column of Heparin 5PW

The resulting Sample 7 was diluted with 41 ml of 50 mM BisTris-HCl(pH 6.0) containing 0.1% CHAPS, and applied to a Heparin affinity column (Heparin 5PW, 0.5×5 cm, Tosoh Corporation) equilibrated with 50 mM BisTris-HCl containing 0.1% CHAPS (pH 6.0). After washing the column with 50 mM BisTris-HCl (pH 6.0) containing 0.1% CHAPS, the adsorbed protein was eluted with a linear gradient of 0.2 to 0.8 M NaCl over 120 minutes at a flow rate of 0.5 ml/min and fractions of 1 ml in size were collected. Using 10 μl of the each of fraction, ADIF activity was measured according to the method described in Example 2. A fraction (16 ml) eluted at NaCl concentrations from about 0.2 to 0.3 M was found to have ADIF activity and was designated as Sample 8.

viii) Purification on a Column of Polycat A

Figure 1:
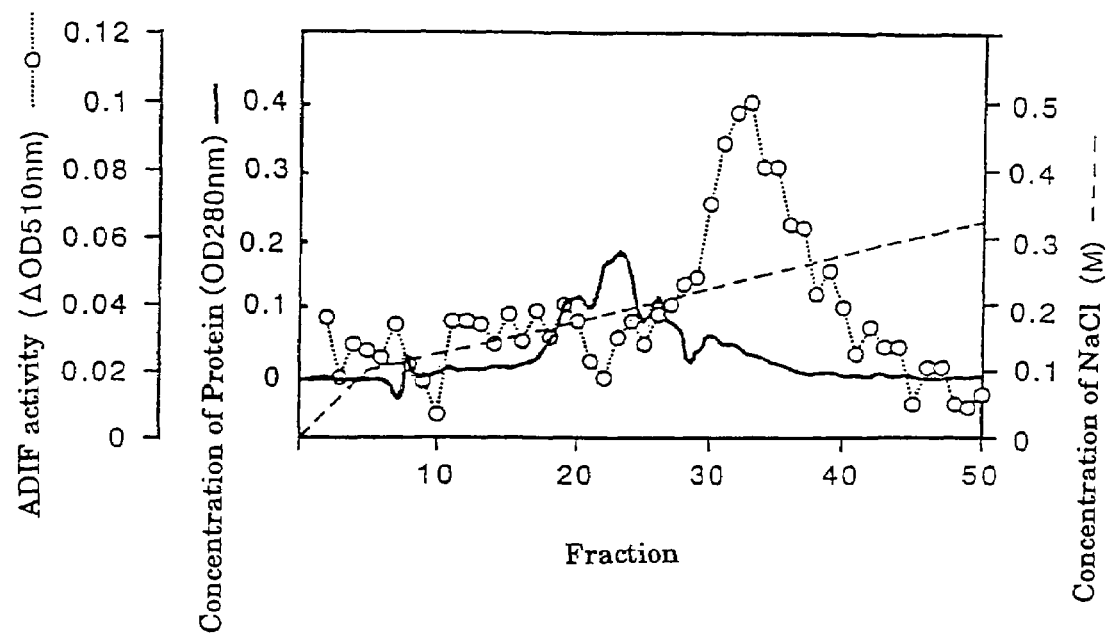
FIG. 1 shows the elution profile of crude ADIF protein (Superose 12 fraction in Example 3, vii); Sample 7) from heparin 5PW column.
Figure 2:
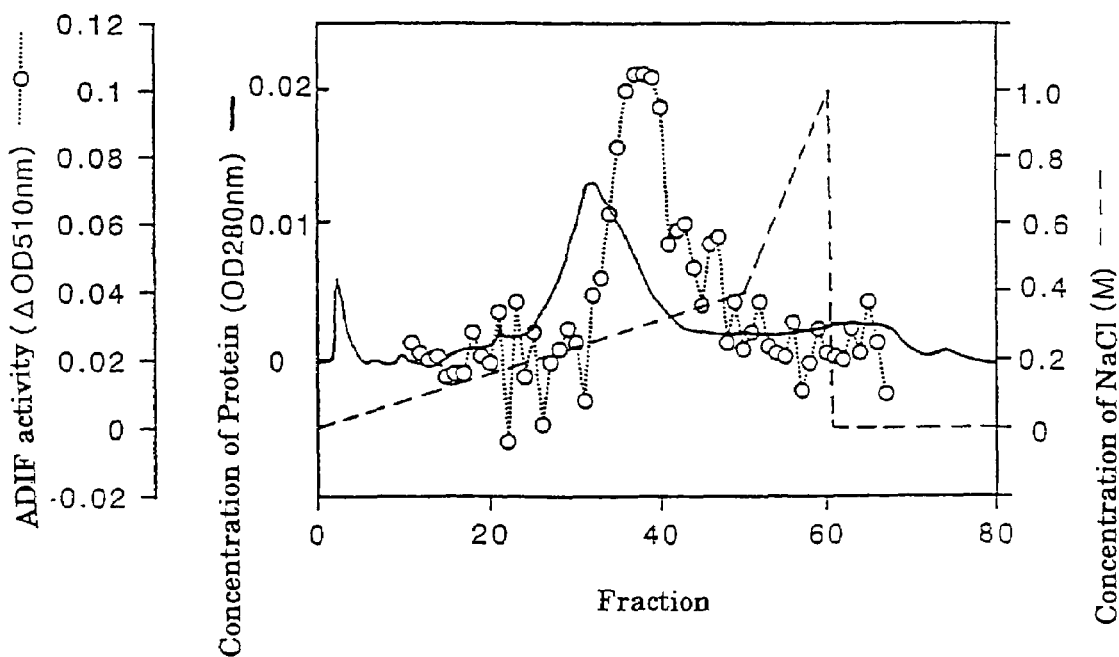
FIG. 2 shows the elution profile of crude ADIF protein (heparin 5PW fraction in Example 3, viii); Sample 8) from Polycat-A column.

The resulting Sample 8 was concentrated using a centrifugal concentrator (Centricon 10, manufactured by Millipore Co.) to about 300 μl, diluted with 600 μl of 50 mM Bis Tris-HCl containing 0.1% CHAPS (pH 6.0) and applied to a weak cation exchange column (Polycat A, 0.46×20 cm, Poly LC Co.) equilibrated. After washing the column with 50 mM BisTris-HCl (pH 6.0) containing 0.1% CHAPS, the adsorbed protein was eluted with a linear gradient of 0 to 0.4 M NaCl over 50 minutes at a flow rate of 1.0 ml/min and fractions of 1 ml in size were collected(FIG. 2). Using 10 μl of the each fraction, ADIF activity was measured according to the method described in Example 2. A fraction from fraction number 37 to 46 eluted at NaCl concentrations from about 0.3 to 0.4 M NaCl was found to have ADIF activity.

ix) Purification on a Reverse Phase Column

Figure 3:
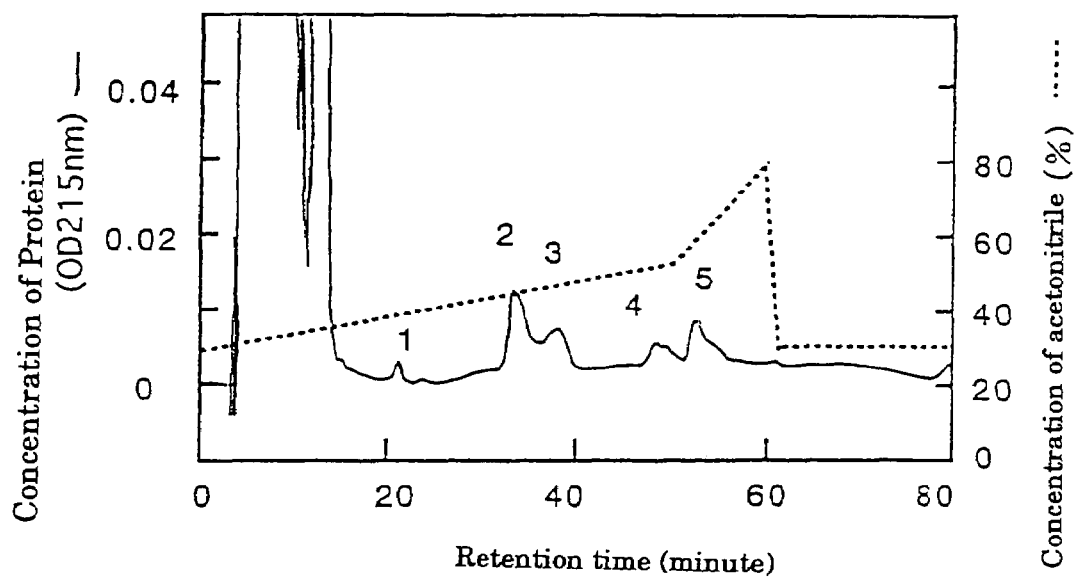
FIG. 3 shows the elution profile of ADIF protein (Polycat-A fractions in Example 3, ix)) from a reverse phase column.
Figure 4:
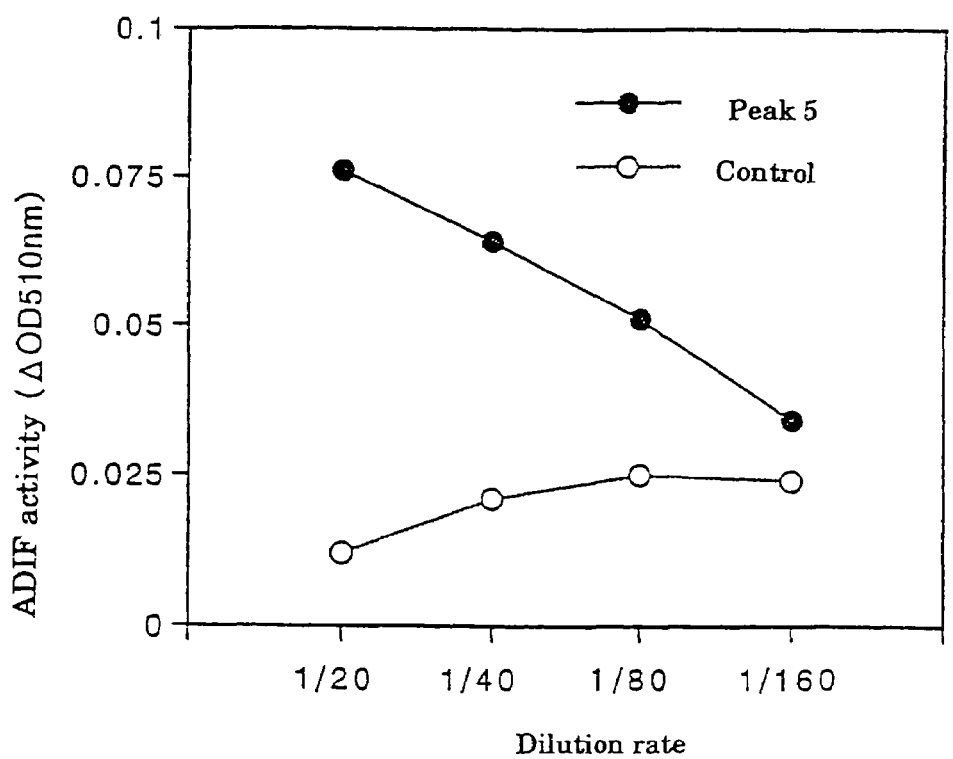
FIG. 4 shows an ADIF activity of peak 5 fraction eluted from a reverse phase column.

One ml of the resulting Polycat A fraction No. 43 was acidified with 10 μl of 20% TFA (trifluoroacetic acid) and was applied to a reverse phase column (C4, 2.1×250 mm, VYDAC Co.) which was equilibrated with 30% acetonitrile containing 0.1% TFA. The adsorbed protein was eluted with a linear gradient of 30 to 55% acetonitrile over 50 minutes at a flow rate of 0.2 ml/min, the each protein peak was collected (FIG. 3). The ADIF activity was measured according to the method described in Example 2 using 35 µl of the each peak fraction. The peak 5 exhibits a concentration-depending ADIF activity. The results are shown in FIG. 4.

Example 4

(Determination of Molecular Weight of ADIF Protein)

Figure 5:
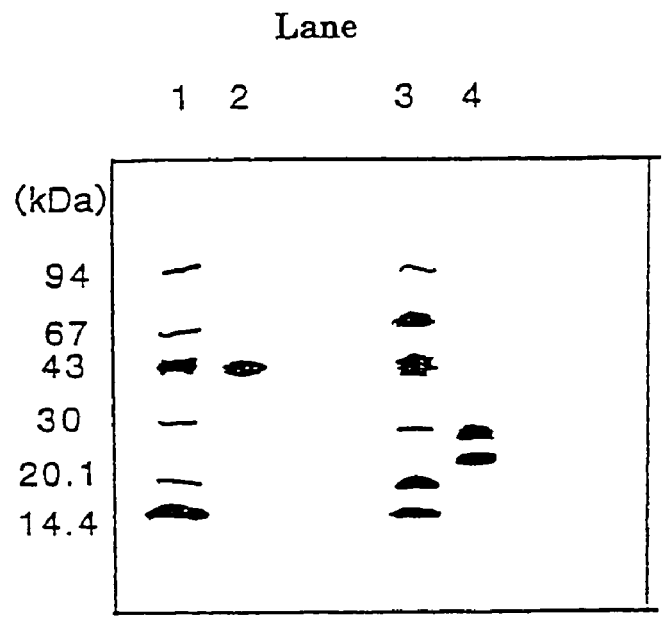
FIG. 5 shows the SDS-polyacrylamide gel electrophoresis of the finally purified ADIF protein under reducing and non-reducing conditions.

One hundred µl of the fraction at peak 5 exhibiting the ADIF activity was subjected to SDS-polyacrylamide gel electrophoresis under reducing and non-reducing conditions. Specifically, 50 µl of peak 5 fraction was concentrated under vacuum and dissolved in 1.5 µl of 10 mM Tris-HCl (pH 8) containing 1 mM EDTA, 2.5% SDS, and 0.01% bromophenol blue, and incubated at 37° C. overnight under reducing conditions (in the presence of 5% 2-mercaptoethanol) or under non-reducing conditions at 37 overnight, and each 1 µl of sample was analysed by SDS-polyacrylamide gel for electrophoresis. The electrophoresis was carried out using gradient gel of 10-15% acrylamide (Amasham Pharmacia Biotech Co.) and electrophoresis device Phast System (Amasham Pharmacia Biotech Co.). Phosphorylase b (94 kDa), bovine serum albumin (67 kDa), ovalbumin (43 kDa), carbonic anhydrase (30 kDa), trypsin inhibitor (20.1 kDa), and α-lactalbumin (14.4 kDa) were used as molecular weight markers. After electrophoresis, silver staining was carried out using Phast Gel Silver Stain Kit (Amasham Pharmacia Biotech Co.). The molecular weight of the peak 5 protein was determined as follows. Specifically, the distance moved from the upper end of the separation gel was measured when each molecular weight marker was subjected to electrophoresis. A standard straight line was produced by plotting the moved distance of each marker against the molecular weight (in logarithm). The molecular weight of the peak 5 protein was determined by applying the measured moving distance of the protein to the standard straight line. The results are shown in FIG. 5. As can be seen from the results, only a 45 kDa protein band was detected under non-reducing conditions, and protein bands at about 28 kDa and 23 kDa were detected under reducing conditions.

Example 5

(Removal of N-Binding Type Sugar Chains from ADIF and Determination of Molecular Weight)

A sample containing about 0.2 µg of ADIF purified by using the reverse phase column according to the method of Example 3, ix) was concentrated under vacuum. One µl of 0.5 M sodium phosphate buffer (pH 8.6), 1 µl of 0.5 M 2-mercaptoethanol, 1 µl of water, and 1 µl of 250 U/ml of N-glycanase solution (Genzyme Co.) were added to the sample. The mixture was thoroughly stirred and incubated at 37° C. for 24 hours. After the addition of 2 µl of 20 mM Tris-HCl buffer (pH 8.0) containing 2 mM EDTA, 5% SDS, 0.02% bromophenol blue, and 5% 2-mercaptoethanol, the mixture was thoroughly stirred and incubated at 37° C. for 24 hours. One µl of the resulting sample was subjected to SDS polyacrylamide gel electrophoresis according to the method of Example 4, followed by silver staining. As a control, 0.2 µg of untreated ADIF prepared according to the method described in Example 3, ix) was subjected to the same electrophoresis and silver staining. The results are shown in FIG. 6. As a result, the apparent molecular weight of the ADIF protein which does not contain N-binding type sugar chains measured by SDS-PAGE under reducing conditions was about 18 kD. Since the apparent molecular weight of the untreated ADIF protein measured by SDS-PAGE under reducing conditions was about 23 kD and/or 28 kD, the ADIF was proven to be a glycoprotein containing N-binding type sugar chains in the molecule. The difference between 23 kD and 28 kD in the apparent molecular weights of the untreated ADIF protein measured by SDS-PAGE under reducing conditions can be considered to be due to the binding number of N-binding type sugar chains.

Example 6

(Determination of N-Terminal Amino Acid Sequence)

The sample of the Polycat A fractions Nos. 37-46 obtained in Example 3, viii) was concentrated using a centrifugal concentrator (Centricon 10, Millipore Co.) to about 500 µl, acidified with 10 µl of 20% TFA and applied to a reverse phase column (C4, 2.1×250 mm, VYDAC Co.) equilibrated with 30% acetonitrile containing 0.1% TFA. The adsorbed protein was eluted with at a linear gradient of 30 to 55% acetonitrile over 50 minutes at a flow rate of 0.2 ml/min and the protein fraction corresponding to peak 5 was collected. The resulting peak 5 was concentrated under vacuum using a centrifugal concentrator. The concentrated fraction was dissolved in 0.5 µl of 10 mM Tris-HCl (pH 8) containing 1 mM EDTA, 2.5% SDS, and 0.01% bromophenol blue, and incubated under reducing conditions (in the presence of 5% 2-mercaptoethanol) at 37° C. overnight, and 4 µl of the fraction was applied to SDS-polyacrylamide gel for electrophoresis. The electrophoresis was carried out using gradient gel of 10-15% acrylamide (Amasham Pharmacia Biotech Co.) in a electrophoresis device Phast System (Amasham Pharmacia Biotech Co.). After the electrophoresis, the protein was transferred onto a PVDF membrane (ProBlot, Perkin Elmer Co.) at 20 V and 25 mA using a blotting device Phast Transfer (Amasham Pharmacia Biotech Co.). After the transfer, the protein was stained with a 2% Coomassie blue/40% methanol/10% acetic acid solution, and destained with a 60% methanol solution to remove excessive colors. Bands of about 23 kDa and 28 kDa were cut out, and subjected to the N-terminal amino acid sequence analysis using a protein sequencer (Procise, 492 type, manufactured by Perkin Elmer Co.) The results are shown in Sequence Table, Sequence ID No. 1.

The each fraction from 37 to 46 of Polycat A fractions obtained in the same manner as described above from about 80 l of IMR-90 culture medium was acidified with 10 µl of 20% TEA and was applied to a reverse phase column (C4, 2.1×250 mm, VYDAC Co.) equilibrated with 30% acetonitrile containing 0.1% TFA ten times. The adsorbed protein was eluted with a linear gradient of 30 to 55% acetonitrile over 55 minutes at a flow rate of 0.2 ml/min, and the protein fraction corresponding to peak 5 was collected. The resulting peak 5 protein was pyridylethylated in reducing conditions and subjected to the N-terminal amino acid sequence analysis using a protein sequencer (Procise, 492 type, manufactured by Perkin Elmer Co.) As a result, an amino acid sequence from the N-terminal to $40^{th}$ amino acid could be determined. The results are shown in Sequence Table, Sequence ID No. 2.

Example 7

(Cloning of ADIF cDNA Fragments)

i) Isolation of poly(A)+RNA from IMR-90 Cells

About 10 μg of poly(A)+RNA was isolated from $1 \times 10^8$ IMR-90 cells using Fast Truck mRNA isolation kit (manufactured by Invitro Gene Co.) according to the manual of the kit.

ii) Preparation of Mixed Primer

The following two mixed primers were synthesized based on the N-terminal amino acid sequence obtained in Example 6 and described in Sequence Table, Sequence ID No. 2. Specifically, all the oligonucleotides (mixed primer, TAE/F) can code for the amino acid sequence from the 13$^{th}$ residue (Thr) to 19$^{th}$ residue (Cys) from the N-terminal was synthesized. In addition, all the complementary oligonucleotides (mixed primer, CFE/R) can code for the amino acid sequence from the 29$^{th}$ residue (Gly) to 35$^{th}$ residue (Glu) from the N-terminal was synthesized. The base sequences of the mixed primers used are shown in Table 1.

TABLE 1

| TAF/F= | ACT | GCT | GAA | ATT | CAA | CAC | TG | SEQ ID No. 21 |
|---|---|---|---|---|---|---|---|---|
|  | C | C | G | C | G | T |  |  |
|  | A | A |  | A |  |  |  |  |
|  | G | G |  |  |  |  |  |  |
| CFE/R= | TC AAA | ACA | CTC | AAA | AAC | ACC | SEQ ID No. 22 |  |
|  | G | G | T | G | G | G |  |  |
|  |  |  |  |  | C | C |  |  |
|  |  |  |  |  | T | T |  |  | iii) Amplification of ADIF cDNA Fragments by PCR

A single strand cDNA was generated using the Superscript II cDNA synthesis kit (Gibco BRL Co.) and 1 μg of poly (A)+RNA obtained in Example 7, i) according to the protocol of Gibco BRL Co. The DNA fragment encoding ADIF was obtained by PCR using the cDNA and template and the primers described in Example 8, ii). The composition of the reaction solution is as follows.

| 10× Ex Taq buffer (Takara Shuzo Co., Ltd.) | 10 μl |
|---|---|
| 2.5 mM dNTP | 8 μl |
| cDNA solution | 2.5 μl |
| Ex Taq (Takara Shuzo Co., Ltd.) | 1 μl |
| Distilled water | 73.5 μl |
| 20 μM primer TAE/F | 2.5 μl |
| 20 μM primer CFE/R | 2.5 μl |

The above solutions were mixed in a microcentrifugal tube and PCR was performed under the following conditions. After pretreatment at 95° C. for 3 minutes, a 3 step reaction consisting of the steps at 95° C. for 30 seconds, at 50° C. for 30 seconds, and at 72° C. for one second was repeated 40 times. Then, the reaction mixture was incubated for five minutes at 72° C. A portion of the reaction mixture was analyzed by agarose gel electrophoresis, and about 68 bp cDNA fragment which was anticipated from the N-terminal amino acid sequence was acidified.

Example 8

(Cloning of the ADIF cDNA Fragment Amplified by PCR and Determination of its DNA Sequence)

The cDNA fragment obtained in Example 7, iii) was inserted into pT7 Tvector (Novagen Co.) using a DNA ligation kit Ver. 2 (Takara Shuzo Co., Ltd.) and *Escherichia coli* XL2Blue (Stratagene Co.) was transformed with the ligation reaction. The resulting transformants were amplified and the plasmid containing ADIF cDNA (about 68 bp) was purified according to a conventional method. This plasmid was named pBSADIF. The sequence of ADIF cDNA in this plasmid was determined by using a DNA sequencing kit (Perkin Elmer). The amino acid sequence of 23 amino acids predicted from this sequence could be found in the N-terminal amino acid sequence (Sequence Table, Sequence ID No. 2) of ADIF which was used for designing the mixed primers. Based on the above results, the cloned 68 bp cDNA was confirmed to be an ADIF cDNA fragment.

Example 9

(Preparation of DNA Probe)

The ADIF cDNA fragment was amplified by PCR under the conditions of Example 6, iii) using the plasmid inserted the 68 bp ADIF cDNA fragment prepared in Example 8 as a template. The ADIF cDNA fragment with about 68 bp was subjected to a preparative agarose gel electrophoresis, and was purified using a QIAEXIIDNA isolation kit (Qiagen Co.). This cDNA was labeled with [α32P]dCTP plasmid using a megaprime DNA labeling kit (Amasham Pharmacia Biotech Co.) and used as a probe for screening the full length of ADIF cDNA.

Example 10

(Preparation of cDNA Library)

cDNA was synthesized using 2.5 μg of the poly(A)+RNA obtained in Example 7, i) oligo (dT) primer, and the Greatlength cDNA synthesis kit (manufactured by Clonetech Co.) according to the protocol of Clonetech Co., Eco RI-Sal I-Not I adapter was ligated to the cDNA and cDNA was separated by size-fractionation. The purified cDNA was precipitate with ethanol and dissolved in 10 μl of a TE buffer solution. The resulting cDNA with adaptor (0.1 μl) was inserted by T4DNA ligase into a λZAP express vector (Stratagene Co.) which had previously been digested with Eco RI. The resulting recombinant phage DNA containing the cDNA was in vitro packaged using Gigapack Gold II (Stratagene Co.) and recombinant a λZAP express phage library was prepared.

Example 11

(Screening of Recombinant Phage)

The recombinant phage obtained in Example 10.was infected with *Escherichia coli* XL1-Blue MRF (Stratagene Co.) for 15 minutes at 37° C. The infected *Escherichia coli* cells were containing added to an NZY medium at 50° C. containing 0.7% agar and plated on the NZY agar plates. After incubation at 37° C. overnight, Hybond N (Amarsham Pharmacia Biotech Co.)was attached to the surface of the plate containing Plague for about 30 minutes. The filter was denatured in alkali solution, neutralized, and washed in 2×SSC according to a conventional method. The phage DNA was immobilized on the filter by UV cross-link (Stratagene Co.). The filter was incubated in a rapid hybridization buffer containing 100 μg/ml of salmon sperm DNA(Amasham Co.) at 65° C. for 1 hour and then incubated overnight in the same buffer containing $2 \times 10^5$ cpm/ml denatured DNA probe prepared in Example 9. After the reaction, the filter was washed twice with 2×SSC, twice with 0.1×SSC, and twice with a 0.1% SDS solution, each at 65° C. for 10 minutes. The washed filter was attached to an X ray film and allowed to stand overnight at −80° C. Positive clones were selected by developing the X ray film. Some positive clones obtained were-purified by screening once more. Among these clones, those containing about 2.0 kb DNA insert were used in the following experiments. The purified phage and helper phage ExAssisi (Stratagene Co.) were infected to *Escherichia coli* XL1-Blue MRF' (Stratagene Co.) using a λZAP express cloning kit (Stratagene Co.) according to the protocol of the Stratagene Co. The culture broth of infected XL1-Blue MRF' was prepared. The broth containing the excised pharge mids was infected to the *Escherichia coli* XLOLR (Stratagene Co.) and the transformant hovering the plasmid containing pBKADIF which consists of pBKCMV (Stratagene Co.) with the above-mentioned 2.0 kb insert was obtained by picking up kanamycin resistant colonies. The transformant was deposited to National Institute of Bioscience and Human-Technology, Agency of Industrial Science and Technology, the Ministry of International Trade and Industry, on Aug. 11, 1998, with the deposition number FERM BP-6459 under the name of XLOLR/pBKADIF. The transformant stock having this plasmid was amplified and the plasmid was purified according to the standard protocol.

Example 12

(Determination of the Nucleotide Sequence of ADIF cDNA Encoding the Full Coding Region)

The nucleotide sequence of ADIF cDNA obtained in Example 11 was determined using a DNA sequencing kit (Perkin Elmer Co.). The used primers were T3, T7 primers (Stratagene Co.) and synthetic primers designed according to the ADIF cDNA sequence, of which the sequences are shown Sequence Table, Sequence ID Nos. 4-11. The nucleotide sequence of ADIF cDNA determined in this manner and the corresponding amino acid sequence predicted by the cDNA sequence are shown in the Sequence No. 12 and No. 13 of the Sequence Table respectively.

Example 13

(Production of Recombinant ADIF from 293/EBNA Cells)

i) Construction of the Plasmid for Expressing ADIF

The plasmid pBKADIF obtained in Example 10 was digested with restriction enzyme, SalI. The ADIF cDNA insert was cut out, separated by agarose gel electophoresis, and purified using an QIAEXIIDNA isolation kit (Qiagen Co.). The purified ADIF cDNA was ligated using a ligation kit Ver. 2 (Takara Shuzo Co., Ltd.) to the expression plasmid pCEP4 (Inviro Gene Co.) previously digested with restriction enzyme Xho I and treated with alkaline phosphatase *E. coli* DH5a (Gibco BRL Co.) was transformed with the ligation mixture. The resulting transformants were grown and the plasmid pCEPADIF containing the ADIF cDNA was purified using QIAGEN Plasmid Midi Kit (Qiagen Co.). The ADIF expression plasmid pCEPADIF was precipitated with ethanol and the precipitate was dissolved in sterilized distilled water to be used for the following experiments.

ii) Transient Expression of ADIF cDNA and Analysis of the Biological Activity of Recombinant ADIF Recombinant ADIF was produced using the ADIF expression plasmid pCEPADIF prepared in Example 13, i) according to the following method and its biological activity was measured $2\times10^5$ 293/EBNA cells (Invitro Gene Co.) were suspended in IMDM (Gibco BRL Co.) containing 10% fatal bovine serum (Gibco BRL Co.) and inoculated in each well of a 24-well plate. Next day, pCEPADIF and a transfection reagent FuGENE™6 (Roche Diagnostic Co.) previously diluted with an IMDM were mixed, and the mixture was added to the cells in each well according to the manufactures protocol attached to the FuGENE™6. 0.5 mg of the pCEPADIF and 1 µl of FuGENE™6 were used for each transfection. After 72 hours, the conditioned medium was harvested and used for determination of the ADIF activity. The ADIF activity was determined by the following method. Specifically, formation of adipocytes induced by dexamethasone was measured by means o-f triglyceride accumulation using a mouse pre-adipocyte MC3T3-G2/PA6 as target cells to determine the suppressing activity. More specifically, 50 µl of the sample diluted with α-MEM (Gibco BRL) containing 10% fatal bovine serum was put in a 96 well microtiter plate, and mouse pre-adipocyte MC3T3-G2/PA6 cells ($3\times10^3$), suspended in 50 µl of α-MEM containing $2\times10^{-7}$ M dexamethasone and 10% fatal bovine serum, were inoculated into the microtiter plate and incubated for one week under the conditions of 5% $CO_2$ at 37° C. and 100% humidity. After seven days, the medium was removed by aspiration and the cells were air-dried to measure the amount of triglyceride accumulated in the adipocytes using a triglyceride assay kit (Triglyceride G-Test Wako, Code No. 274-69802, made by Wako Pure Chemicals Co., Ltd.). The decrease of OD at 510 nm was taken as the ADIF activity. As a result, as shown in Table 2, the culture broth of 293/EBNA cells transfected with ADIF gene was confirmed to exhibit the same activity as natural ADIF previously obtained from the culture broth of IMR-90.

TABLE 2

| Rate of dilution | 1/4 | 1/8 | 1/16 | 1/32 | 1/64 |
| --- | --- | --- | --- | --- | --- |
| ADIF gene transfected | 0.141 | 0.130 | 0.109 | 0.089 | 0.067 |
| Vector transfected | −0.009 | 0.009 | −0.007 | 0.005 | 0.015 |
| Untreated | 0.001 | 0.009 | −0.018 | 0.013 | 0.016 |

(Decrease of OD at 510 nm, Δ510 nm)

Example 14

(Determination of ADIF Activity Using 3T3/LI Cells)

The ADIF activity was evaluated by estimating the suppression effects of adipogenesis induced by dexamethasone and 1-methyl-3-isobutyl xanthine with triglyceride accumulation using a mouse precursor pre-adipocyte 3T3-LI cells (Deposited with ATCC, Deposition No. CL173) as target cells. Specifically, 50 µl of the sample diluted with α-MEM (Gibco BRL) containing 10% fatal bovine serum was put in a 96 well microtiter plate, and mouse pre-adipocyte stock 3T3-LI cells ($5\times10^3$) were suspended in 50 µl of α-MEM medium containing $4\times10^{-7}$ M dexamethasone, $2\times10^{-5}$ M 1-methyl-3-isobutyl xanthine, and 10% fatal bovine serum, inoculated into the microtiter plate and incubated for one week under the conditions of 5% $CO_2$ at 37° C. and 100% humidity. After seven days, the medium was removed by aspiration and the cells were air-dried to measure the amount of triglyceride accumulated in the adipocytes using a triglyceride assay kit (Triglyceride G-Test Wako, Code No. 274-69802, made by Wako Pure Chemicals Co., Ltd.). The decrease of OD at 510 nm was taken as the ADIF activity. As a result, as shown in Table 3, the culture broth of 293/EBNA cells transfected with ADIF gene was also confirmed to exhibit the ADIF activity when the 3T3-LI cells were used as target cell.

TABLE 3

| Rate of dilution | 1/4 | 1/8 | 1/16 | 1/32 | 1/64 |
|---|---|---|---|---|---|
| ADIF gene transfected | 0.106 | 0.103 | 0.079 | 0.065 | 0.053 |
| Vector transfected | −0.042 | −0.021 | 0.013 | 0.011 | 0.010 |
| Untreated | 0.045 | −0.034 | 0.002 | −0.030 | −0.004 |

(Decrease of OD at 510 nm, Δ510 nm)

Example 15

Preparation of ADIF-FLAG(+Xho I)

(I) Addition of Restriction Enzyme XhoI Recognizing Sequence and FLAG Encoding Sequence A sequence which recognizes restriction enzyme XhoI and a sequence encoding FLAG were added to immediately after the sequence encoding the $265^{th}$ Arg which is the C-terminal of ADIF amino acid sequence described in the Sequence ID No. 13. Ten amino acids, Leu, Glu, Asp, Tyr, Lys, Asp, Asp, Asp, Asp, and Lys (L-E-D-Y-K-D-D-D-D-K; Sequence ID No. 20), are added after the $265^{th}$ Arg by this sequence. The mutagenesis was performed by the PCR method. The sequences of primers used for the mutagenesis are shown in Table 4 and Sequence ID Nos. 14-19.

TABLE 4

ADFY1Hd
5'-GGGGGAAGCTTGCGGCGAAGGAGGAAGAGG-3'
ADFL2R
5'-GGCTCGAGGGCATGGGCGTTTGGGTGG-3'
ADFL3R
5'-GGCTCGAGTGCTTCCCCGTGGTGGGCC-3'
ADFL4R
5'-GGCTCGAGGGTGCAGAAGCTCAAGATG-3'
ADFL5R
5'-GGCTCGAGCCCACAGGTCAGCAGCAAG-3'
ADFL6R
5'-GGGGGCTCGAGGTTCTCCTGGGCAGCCGCGCACAG-3'

PCR was carried out under the following conditions.

After the reaction for 3 minutes at 95° C., 1 minute at 55° C., and 3 minutes at 72° C., a 3 step reaction consisting of the reactions for one minute at 96° C., one minute at 55° C., and three minutes at 72° C. was repeated 25 times. Then, the reaction mixture was incubated for five minutes at 72° C. The composition of the PCR reaction solution are shown below.

The PCR Reaction Solution for Mutagenesis

| | |
|---|---|
| Ex Taq polymerase (Takara Shuzo Co., Ltd.) | 0.5 μl |
| 10× Ex Taq buffer (Takara Shuzo Co., Ltd.) | 10 μl |
| 2.5 mM dNTP solution | 8 μl |
| Template plasmid vector (pCEPADIF 40 ng/μl) | 1 μl |
| 0.1 M primer (ADFY1 Hd) | 1 μl |
| 0.1 M primer (ADFLSXR) | 1 μl |
| Sterilized distilled water | 78.5 μl |

The DNA obtained by PCR was separated by agarose gel electrophoresis and extracted with 20 μl of sterilized distilled water using QIAEXII Gel Extraction kit (Qiagen Co.). Ten μl of a solution containing the extracted DNA was treated with restriction enzyme Hind III (Takara Shuzo Co., Ltd.) and Sal I (Takara Shuzo Co., Ltd.) to digest the DNA. The DNA solution was subjected to electophoresis using 1.5% agarose gel and the target DNA fragment was extracted with 20 μl of sterilized distilled using QIAEXII Gel Extraction kit (DNA Solution 1).

(II) Construction of ADIF-FLAG(+Xho I) Expression Vector pCEP4 was digested with restriction enzyme Hind III and Xho I (Takara Shuzo Co., Ltd.) and was subjected to electrophoresis using 1.0% agarose gel. A DNA fragment with an about 10 kbp was extracted using QIAEXII Gel Extraction kit (DNA Solution 2).

Four μl of DNA ligation kit Ver. 2I solution (Takara Shuzo Co., Ltd.) was added to 3 μl of DNA Solution 1 and 1 μl of DNA Solution 2, and the mixture was subjected to a ligation reaction while maintaining at 16° C. for 30 minutes. *Escherichia coli* DH5α was transformed using the resultant reaction solution. The DNA structure of the transformed *Escherichia coli* which was ampicillin resistant was analyzed to select the transformants possessing the target plasmid. The analysis of DNA structure was carried out by measuring the length of fragment obtained by digestion with restriction enzyme and determining the DNA sequence. The expression vector obtained was named pCEP4 ADIF-FLAG (+Xho I).

(III) Preparation of Mutant Expression Vector

*Escherichia coli* having pCEP4-ADIF-FLAG(+Xho I) was grown in 25 ml of LB medium (1% bacto-trypton, 0.5% bacto-yeast extracts, 1% NaCl) and purified by QIAGEN Plasmid Midi kit (Qiagen Co.). The expression vector was precipitated with ethanol and the precipitate was dissolved in 50 μl of sterilized distilled water to be used for the following experiment.

Example 16

(Preparation of C-Terminal Deletion Mutant)

(I) Mutagenesis of C-Terminal Deletion Mutant

Mutants having the same amino acid sequence as the Sequence ID No. 13, but deleted for the sequences from $236^{th}$ Arg to $265^{th}$ Arg, from $206^{th}$ Gly to $265^{th}$ Arg, from $176^{th}$ Ser to $265^{th}$ Arg, from $146^{th}$ Glu to $265^{th}$ Arg, or from $116^{th}$ Thr to $265^{th}$ Arg were prepared. The mutants with deletion of the sequences from $236^{th}$ Arg to $265^{th}$ Arg, from $206^{th}$ Gly to $265^{th}$ Arg, from $176^{th}$ Ser to $265^{th}$ Arg, from $146^{th}$ Glu to $265^{th}$ Arg, and from $116^{th}$ Thr to $265^{th}$ Arg were respectively named ADIF-R1, ADIF-R2, ADIF-R3, ADIF-R4, and ADIF-R5.

Mutagenesis for the preparation of the mutants was carried out by the PCR method. The primers used for mutagenesis are shown in Table and the sequences of the primers are shown in the sequence ID Nos. PCR was carried out under the following conditions. After the reaction for 3 minutes at 97° C., 1 minute at 55° C.; and 3 minutes at 72° C., a 3 step reaction consisting of the reactions for one minute at 96° C., one minute at 55° C., and three minutes at 72° C. was repeated 25 times. Then, the reaction mixture was incubated for five minutes at 72° C. The composition of the PCR reaction solution are shown below.

The PCR reaction solution for C-terminal deletion mutagenesis

| | |
|---|---|
| Ex Taq polymerase (Takara Shuzo Co., Ltd.) | 0.5 μl |
| 10× Ex Taq buffer (Takara Shuzo Co., Ltd.) | 10 μl |
| 2.5 mM dNTP solution | 8 μl |
| Template plasmid vector (pCEPADIF 40 ng/μl) | 1 μl |
| 0.1 M primer (ADFY1 Hd) | 1 μl |
| 0.1 M mutagenesis primer | 1 μl |
| Sterilized distilled water | 78.5 μl |

The DNA obtained by the PCR method was separated by agarose gel electophoresis and extracted with 20 μl of sterilized distilled water using QIAEXII Gel Extraction kit. Ten μl of a solution containing the extracted DNA was treated with restriction enzyme Hind III and Sal I to digest the DNA. The DNA solution was subjected to electophoresis using 1.5% agarose gel and the target DNA fragment was extracted with 20 μl of sterilized distilled water using QIAEXII Gel Extraction kit (DNA Solution 3).

(II) Construction of Mutant Expression Vector pCEP4-ADIF-FLAG(+Xho 1) was digested with restriction enzyme Hind III and Xho I and subjected to electophoresis using 1.0% agarose gel. A DNA fragment with a length of about 10 kbp was extracted using QIAEXII Gel Extraction kit (DNA Solution 4).

Four μl of DNA ligation kit Ver. 2I solution was added to 3 μl of DNA Solution 3 and 1 μl of DNA Solution 4, and the mixture was subjected to a ligation reaction while maintaining at 16° C. for 30 minutes. *Escherichia coli* DH5α was transformed using the resultant reaction solution. The DNA structure of the transformed *Escherichia coli* which was ampicillin resistant was analyzed to select the transformant possessing the target plasmid. The analysis of DNA structure was carried out by measuring the length of fragment obtained by digestion with restriction enzyme and determining the DNA sequence. The expression vectors for ADIF-R1, ADIF-R2, ADIF-R3, ADIF-R4 and ADIF-R5 were respectively named pCEP4-ADIF-R1, pCEP4-ADIF-R2, pCEP4-ADIF-R3, pCEP4-ADIF-R4, and pCEP4-ADIF-R5.

(III) Preparation of Mutant Expression Vector

*Escherichia coli* having the mutant expression vector was grown in 25 ml of LB medium and purified by QIAGEN Plasmid Midi kit. Each expression vector was precipitated with ethanol and the precipitate was dissolved in 50 μl of sterilized distilled water to be used for the following experiment.

Example 17

(Transient Expression of ADIF-FLAG(+Xho I) and Mutant cDNA)

$2 \times 10^6$ 293-EBNA cells were suspended in 20 ml of IMDM containing 10% fetal bovine serum, spread in a 75 cm$^2$ culture flask, and cultured for 24 hours in $CO_2$ at 37° C. One hundred ml of FuGENE6 (Roche Diagonostic) was added to 3.5 ml of serum-free IMDM medium. The mixture was allowed to stand for 5 minutes at room temperature and added dropwise to a solution containing 35 μg of ADIF-FLAG (+Xho I). The resulting mixture was allowed to stand for 15 minutes at room temperature. This mixture was added dropwise to the cells on the five 75 cm$^2$ flasks, 700 μl each, thereby transfecting expression vector into the cells. The same procedure was applied to the other mutant expression vectors. The cells transfected expression vectors were incubated in a $CO_2$ incubator at 37° C. for 24 hours. After culturing, 20 ml of fresh serum-free IMDM was added and the cells were cultured in a $CO_2$ incubator at 37° C. for 48 hours. The culture flasks broth was collected, 20 ml of fresh serum-free IMDM was added to the culture flasks, and the cells were continued to culture in a $CO_2$ incubator at 37° C. for 48 hours. The culture broth was collected and combined with the previously collected culture broth to obtain a total of 200 ml of culture broth.

Example 18

(Purification of ADIF-FLAG(+Xho I) and Mutants)

ADIF-FLAG(+Xho I) and mutants were purified from 200 ml of the culture broth obtained from transient expressed cells. In the purification, ADIF-FLAG(+Xho I) and mutants were specifically adsorbed in and eluted from a gel carrier containing an anti-FLAG antibody (M2, Sigma Co.) as a ligand.

One ml of the gel suspended in TBS/T (50 mM Tris-HCl (pH 7.4), 150 mM NaCl, 0.01% Tween 80 (Sigma Co.))was filled in 8 centrifugal tubes (volume: 50 ml). Twenty five ml of the collected culture broth was added to each tube and the mixture was gently rotated at 4° C. for 24 hours to, cause the ADIF-FLAG(+Xho I) and mutants to be adsorbed to the antibody. Gels precipitated by centrifugation were collected in one centrifugal tube (Volume: 15 ml). The gel was washed by suspending in 10 ml of TBS/T and centrifuging the suspension. After washing three times, the gel was suspended in 5 ml of a elution buffer (0.1 M Glycin-HCl (pH 2.8), 150 mM NaCl, 0.01% Tween 80) and centrifuged to collect the eluted solution. This procedure was repeated to obtain 10 ml of the eluted solution in total. The eluted solution was neutralized with the addition of 100 μl of 3 M Tris. The eluted solution was replaced with a sodium phosphate buffer (10 mM sodium phosphate (pH 7.0), 0.3M NaCl)using Centriplus 10 (Millipore Co.) and the protein concentration was adjusted to 32 μg/ml with the same buffer.

Example 19

(Analysis Using SDS-PAGE)

The purified ADIF-FLAG (+Xho I) and mutants were subjected to SDS-PAGE. The electrophoresis was carried out under reducing conditions using Phast System (Amashan Pharmacia Biotech Co.). The purified ADIF-FLAG(+Xho I) and mutants, 60 ng each, were subjected to 10-15% Gradient gel (Amasham Pharmacia Biotech Co.) for electrophoresis.

As a result, each molecular weight of ADIF-FLAG(+Xho I) and mutants was almost consistent with that predicated from nucleotide sequences. The purity was more than 90%.

Example 20

(Measurement of Activity)

3T3-L1 cells suspended in DMEM containing 10% fetal bovine serum (DMEM-FCS) at a concentration of $5 \times 10^4$ cells/ml were inoculated into a 96-well plate in the amount of 100 μl/well, and cultured in a $CO_2$ incubator for 96 hours at 37° C. To differentiate confluent cells into adipocytes, the medium in the 96-well plate was replaced with DMEM-FCS containing $5 \times 10^{-4}$ M 1-methyl-3-isobutyl xanthine and $1 \times 10^{-6}$ M dexamethasone and cells were cultured for 48 hours in a CO$_2$ incubator at 37° C. DMEM-FCS was added to the culture media to make the concentrations of ADIF-FLAG(+Xho I) or the mutants from 200 ng/ml to 6.4 μg/ml. After the culture for 48 hour, the medium was removed and 100 μl of DMEM-FCS containing ADIF-FLAG(+Xho I) or the mutants in the same concentration as above was added to each well. The culture was continued in a CO$_2$ incubator at 37° C. for five days, and the cells were differentiated into adipocytes. After culturing, adipogenesis inhibitory activity (ADIF activity) of the cells in the 96-well plate, which was thoroughly dried after removal of the culture broth, was examined using Triglyceride-G Test Wako (Wako Pure Chemicals Co., Ltd.). The decrease of the absorbance found on a sample from the absorbance at 510 nm in the well with no mutants was taken as the ADIF activity of the sample.

The results were shown in FIG. 7. The activity measurement was carried out twice for each sample and the mean value of the two measurements is shown. The mutants ADIF-R1, ADIF-R2 and ADIF-R3 showed almost the same specific activity as ADIF-FLAG (+Xho I). The specific activity of ADIF-R4 was less than ⅓₀ of that of ADIF-FLAG (+Xho I). ADIF-R5 exhibited no ADIF activity even at a concentration of 6.4 μg/ml.

INDUSTRIAL APPLICABILITY

An adipogenesis inhibitory factor (ADIF) which is a novel protein having an activity of suppressing differentiation and/or maturation of adipocytes; a process of producing the protein by culturing human fibroblasts and purifying from the culture broth using an ion exchange column, affinity column, and reverse phase column chromatography; and a process for efficiently producing the protein by culturing the human fibroblasts using alumina ceramic pieces as a cell adhering carrier are provided. A cDNA encoding the protein and a process of producing the protein using the cDNA are also provided. The protein of the present invention is useful as a pharmaceutical composition for preventing or treating obesity or as an antigen for establishing immunological diagnosis.

REMARKS TO DEPOSITED MICROORGANISMS

Name and address of the organization in which the microorganisms have been deposited:

Name: National Institute of Bioscience and Human-Technology, the Agency of Industrial Science and Technology, the Ministry of International Trade and Industries Address: 1-1-3, Higashi, Tsukuba-shi, Ibaraki-ken, Japan (Postal Code: 305-8566).

Date of deposition: Aug. 11, 1998

Number of deposition given by the deposition organization: FERM BP-6459

What is claimed is:

1. A recombinant C-terminal deletion mutant protein having adipogenesis inhibitory activity, wherein the wild-type full-length protein to be truncated by C-terminal deletion is a polypeptide consisting of SEQ ID NO: 13, wherein said recombinant C-terminal deletion mutant protein having adipogenesis inhibitory activity comprises amino acid residues 1-175 of SEQ ID NO: 13.

2. A recombinant polypeptide consisting of amino acid residues 1-265 of SEQ ID NO: 13.

3. A recombinant polypeptide consisting of amino acid residues 1-235 of SEQ ID NO: 13.

4. A recombinant polypeptide consisting of amino acid residues 1-205 of SEQ ID NO: 13.

5. A recombinant polypeptide consisting of amino acid residues 1-175 of SEQ ID NO: 13.

6. An isolated polypeptide consisting of amino acid residues 1-265 of SEQ ID NO: 13.

7. A method of producing the polypeptide of claim 6, comprising culturing human embryo lung fibroblasts IMR-90 and purifying the polypeptide from the culture broth by chromatography using an ion exchange column, affinity column, and reverse phase column.

8. The method of producing a polypeptide according to claim 7, wherein said culturing human embryo lung fibroblasts IMR-90 is on alumina ceramic pieces.

* * * * *

SEQUENCE LISTING

```
<160> NUMBER OF SEQ ID NOS: 22

<210> SEQ ID NO 1
<211> LENGTH: 20
<212> TYPE: PRT
<213> ORGANISM: Homo Sapiens
<220> FEATURE:
<221> NAME/KEY: MISC_FEATURE
<222> LOCATION: (1)..(2)
<223> OTHER INFORMATION: Xaa = any one amino acid
<220> FEATURE:
<221> NAME/KEY: MISC_FEATURE
<222> LOCATION: (5)..(5)
<223> OTHER INFORMATION: Xaa = any one amino acid
<220> FEATURE:
<221> NAME/KEY: MISC_FEATURE
<222> LOCATION: (9)..(9)
<223> OTHER INFORMATION: Xaa = any one amino acid
<220> FEATURE:
<221> NAME/KEY: MISC_FEATURE
<222> LOCATION: (19)..(19)
<223> OTHER INFORMATION: Xaa = any one amino acid

<400> SEQUENCE: 1

Xaa Xaa Gln Gln Xaa Gly Arg Leu Xaa Leu Gln Asn Thr Ala Glu Ile
1               5                   10                  15

Gln His Xaa Leu
            20

<210> SEQ ID NO 2
<211> LENGTH: 40
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Xaa = any one amino acid
```

```
<220> FEATURE:
<221> NAME/KEY: MISC_FEATURE
<222> LOCATION: (38)..(39)
<223> OTHER INFORMATION: Xaa = any one amino acid

<400> SEQUENCE: 2

Xaa Ser Gln Gln Lys Gly Arg Leu Ser Leu Gln Asn Thr Ala Glu Ile
1               5                   10                  15

Gln His Cys Leu Val Asn Ala Gly Asp Val Gly Cys Gly Val Phe Glu
            20                  25                  30

Cys Phe Glu Asn Asn Xaa Xaa Glu
        35                  40

<210> SEQ ID NO 3
<211> LENGTH: 40
<212> TYPE: PRT
<213> ORGANISM: Homo Sapiens

<400> SEQUENCE: 3

Ser Ser Gln Gln Lys Gly Arg Leu Ser Leu Gln Asn Thr Ala Glu Ile
1               5                   10                  15

Gln His Cys Leu Val Asn Ala Gly Asp Val Gly Cys Gly Val Phe Glu
            20                  25                  30

Cys Phe Glu Asn Asn Ser Cys Glu
        35                  40

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
aattaaccct cactaaaggg                                           20

<210> SEQ ID NO 5
<211> LENGTH: 22
<212> TYPE: DNA
<213> ORGANISM: Artificial Sequence
<220> FEATURE:
<223> OTHER INFORMATION: Synthetic DNA

<400> SEQUENCE: 5
gtaatacgac tcactatagg gc                                        22

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
aagaggggag cacaaaggat                                           20

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA
```

```
<400> SEQUENCE: 7
gtccctgcag aatacagcgg                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
caaggacttg ctgctgcacg                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
tggacggcgt ggaggaaaga                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
gctcaagatg gagcacaggc                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11
gttgtgcaga aaagtcatgc                                                    20

<210> SEQ ID NO 12
<211> LENGTH: 882
<212> TYPE: DNA
<213> ORGANISM: Homo Sapiens

<400> SEQUENCE: 12
atgaccctgg ctttggtgtt ggccaccttt gacccggcgc gggggaccga cgccaccaac        60
ccacccgagg gtccccaaga caggagctcc cagcagaaag ccgcctgtc cctgcagaat        120 acagcggaga tccagcactg tttggtcaac gctggcgatg tggggtgtgg cgtgtttgaa       180
tgtttcgaga caactcttg tgagattcgg ggcttacatg ggatttgcat gacttttctg       240
cacaacgctg gaaaatttga tgcccagggc aagtcattca tcaaagacgc cttgaaatgt      300
aaggcccacg ctctgcggca caggttcggc tgcataagcc ggaagtgccc ggccatcagg      360
gaaatggtgt cccagttgca gcgggaatgc tacctcaagc acgacctgtg cgcggctgcc      420
caggagaaca cccgggtgat agtggagatg atccatttca aggacttgct gctgcacgaa      480
```

```
cctacgtgg acctcgtgaa cttgctgctg acctgtgggg aggaggtgaa ggaggccatc      540
acccacagcg tgcaggttca gtgtgagcag aactggggaa gcctgtgctc catcttgagc      600
ttctgcacct cggccatcca gaagcctccc acggcgcccc ccgagcgcca gccccaggtg      660
gacagaacca agctctccag ggcccaccac ggggaagcag acatcacctc ccagagccc       720 agcagtaggg agactggccg aggtgccaag ggtgagcgag gtagcaagag ccacccaaac      780
gcccatgccc gaggcagagt cgggggcctt ggggctcagg gaccttccgg aagcagcgag      840
tgggaagacg aacagtctga gtattctgat atccggaggt ga                         882
```

<210> SEQ ID NO 13
<211> LENGTH: 293
<212> TYPE: PRT
<213> ORGANISM: Homo Sapiens

<400> SEQUENCE: 13

```
Met Thr Leu Ala Leu Val Leu Ala Thr Phe Asp Pro Ala Arg Gly Thr
1               5                   10                  15

Asp Ala Thr Asn Pro Pro Glu Gly Pro Gln Asp Arg Ser Ser Gln Gln
            20                  25                  30

Lys Gly Arg Leu Ser Leu Gln Asn Thr Ala Glu Ile Gln His Cys Leu
        35                  40                  45

Val Asn Ala Gly Asp Val Gly Cys Gly Val Phe Glu Cys Phe Glu Asn
    50                  55                  60

Asn Ser Cys Glu Ile Arg Gly Leu His Gly Ile Cys Met Thr Phe Leu
65                  70                  75                  80

His Asn Ala Gly Lys Phe Asp Ala Gln Gly Lys Ser Phe Ile Lys Asp
                85                  90                  95

Ala Leu Lys Cys Lys Ala His Ala Leu Arg His Arg Phe Gly Cys Ile
            100                 105                 110

Ser Arg Lys Cys Pro Ala Ile Arg Glu Met Val Ser Gln Leu Gln Arg
        115                 120                 125

Glu Cys Tyr Leu Lys His Asp Leu Cys Ala Ala Ala Gln Glu Asn Thr
    130                 135                 140

Arg Val Ile Val Glu Met Ile His Phe Lys Asp Leu Leu His Glu
145                 150                 155                 160

Pro Tyr Val Asp Leu Val Asn Leu Leu Leu Thr Cys Gly Glu Glu Val
                165                 170                 175

Lys Glu Ala Ile Thr His Ser Val Gln Val Gln Cys Glu Gln Asn Trp
            180                 185                 190

Gly Ser Leu Cys Ser Ile Leu Ser Phe Cys Thr Ser Ala Ile Gln Lys
        195                 200                 205

Pro Pro Thr Ala Pro Pro Glu Arg Gln Pro Gln Val Asp Arg Thr Lys
    210                 215                 220

Leu Ser Arg Ala His His Gly Glu Ala Gly His His Leu Pro Glu Pro
225                 230                 235                 240

Ser Ser Arg Glu Thr Gly Arg Gly Ala Lys Gly Glu Arg Gly Ser Lys
                245                 250                 255

Ser His Pro Asn Ala His Ala Arg Gly Arg Val Gly Gly Leu Gly Ala
            260                 265                 270

Gln Gly Pro Ser Gly Ser Ser Glu Trp Glu Asp Glu Gln Ser Glu Tyr
        275                 280                 285

Ser Asp Ile Arg Arg
    290
```

<210> SEQ ID NO 14
<211> LENGTH: 30
<212> TYPE: DNA
<213> ORGANISM: Artificial Sequence
<220> FEATURE:
<223> OTHER INFORMATION: Synthetic DNA

<400> SEQUENCE: 14
gggggaagct tgcggcgaag gaggaagagg                           30

<210> SEQ ID NO 15
<211> LENGTH: 27
<212> TYPE: DNA
<213> ORGANISM: Artificial Sequence
<220> FEATURE:
<223> OTHER INFORMATION: Synthetic DNA

<400> SEQUENCE: 15
ggctcgaggg catgggcgtt tgggtgg                              27

<210> SEQ ID NO 16
<211> LENGTH: 27
<212> TYPE: DNA
<213> ORGANISM: Artificial Sequence
<220> FEATURE:
<223> OTHER INFORMATION: Synthetic DNA

<400> SEQUENCE: 16
ggctcgagtg cttccccgtg gtgggcc                              27

<210> SEQ ID NO 17
<211> LENGTH: 27
<212> TYPE: DNA
<213> ORGANISM: Artificial Sequence
<220> FEATURE:
<223> OTHER INFORMATION: Synthetic DNA

<400> SEQUENCE: 17
ggctcgaggg tgcagaagct caagatg                              27

<210> SEQ ID NO 18
<211> LENGTH: 27
<212> TYPE: DNA
<213> ORGANISM: Artificial Sequence
<220> FEATURE:
<223> OTHER INFORMATION: Synthetic DNA

<400> SEQUENCE: 18
ggctcgagcc cacaggtcag cagcaag                              27

<210> SEQ ID NO 19
<211> LENGTH: 35
<212> TYPE: DNA
<213> ORGANISM: Artificial Sequence
<220> FEATURE:
<223> OTHER INFORMATION: Synthetic DNA

<400> SEQUENCE: 19
gggggctcga ggttctcctg ggcagccgcg cacag                     35

<210> SEQ ID NO 20
<211> LENGTH: 10
<212> TYPE: PRT
<213> ORGANISM: Artificial Sequence
<220> FEATURE:

<223> OTHER INFORMATION: Synthetic Peptide

<400> SEQUENCE: 20

Leu Glu Asp Tyr Lys Asp Asp Asp Asp Lys
1               5                   10

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = a, c, g, or t
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (9)..(9)
<223> OTHER INFORMATION: n = a or g
<220> FEATURE:
<221> NAME/KEY: misc_feature
<222> LOCATION: (12)..(12)
<223> OTHER INFORMATION: n = a, c, g, or t
<220> FEATURE:
<221> NAME/KEY: misc_feature
<222> LOCATION: (15)..(15)
<223> OTHER INFORMATION: n = a or g
<220> FEATURE:
<221> NAME/KEY: misc_feature
<222> LOCATION: (18)..(18)
<223> OTHER INFORMATION: n = c or t

<400> SEQUENCE: 21
acngcngana tncancantg                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = a or g
<220> FEATURE:
<221> NAME/KEY: misc_feature
<222> LOCATION: (6)..(6)
<223> OTHER INFORMATION: n = a or g
<220> FEATURE:
<221> NAME/KEY: misc_feature
<222> LOCATION: (9)..(9)
<223> OTHER INFORMATION: n = c or t
<220> FEATURE:
<221> NAME/KEY: misc_feature
<222> LOCATION: (12)..(12)
<223> OTHER INFORMATION: n = a or g
<220> FEATURE:
<221> NAME/KEY: misc_feature
<222> LOCATION: (15)..(15)
<223> OTHER INFORMATION: n = a, c, g, or t
<220> FEATURE:
<221> NAME/KEY: misc_feature
<222> LOCATION: (18)..(18)
<223> OTHER INFORMATION: n = a, c, g, or t

<400> SEQUENCE: 22
tcnaancant cnaaacncc                                                     20